United States Patent
Vu et al.

(12) United States Patent (10) Patent No.: US 8,648,900 B2
(45) Date of Patent: Feb. 11, 2014

(54) VIDEO OBSERVATION OF A PATIENT'S FACE DURING A MEDICAL PROCEDURE WHILE THE PATIENT IS IN A PRONE POSITION

(75) Inventors: An Binh Vu, Carlsbad, CA (US); Gregory Philip Jordan, Carlsbad, CA (US)

(73) Assignee: Dupaco, Inc., Oceanside, CA (US)

( * ) Notice: Subject to any disclaimer, the term of this patent is extended or adjusted under 35 U.S.C. 154(b) by 1666 days.

(21) Appl. No.: 11/867,242

(22) Filed: Oct. 4, 2007

(65) Prior Publication Data

US 2009/0093685 A1    Apr. 9, 2009

(51) Int. Cl.
*H04N 7/18* (2006.01)
*H04N 5/225* (2006.01)
*A61B 5/00* (2006.01)

(52) U.S. Cl.
USPC ............ 348/64; 348/77; 348/78; 348/207.99; 600/300

(58) Field of Classification Search
USPC ................... 348/64, 77, 78, 207.99; 600/300
See application file for complete search history.

(56) References Cited

U.S. PATENT DOCUMENTS

| | | | |
|---|---|---|---|
| 4,752,064 A | 6/1988 | Voss | |
| 5,220,699 A | 6/1993 | Farris | |
| 5,278,756 A * | 1/1994 | Lemchen et al. | 600/587 |
| 5,441,047 A * | 8/1995 | David et al. | 600/483 |
| 5,443,058 A | 8/1995 | Ough | |
| 5,878,746 A * | 3/1999 | Lemelson et al. | 600/407 |
| 6,490,737 B1 | 12/2002 | Mazzei et al. | |
| 7,165,860 B1 | 1/2007 | Metzger | |
| 2004/0015191 A1 | 1/2004 | Otman et al. | |
| 2005/0066444 A1 | 3/2005 | Mazzei | |
| 2006/0058590 A1 | 3/2006 | Shaw et al. | |
| 2007/0017534 A1 | 1/2007 | Thorpe | |
| 2007/0132597 A1 * | 6/2007 | Rodgers | 340/573.1 |
| 2009/0044334 A1 * | 2/2009 | Parsell et al. | 5/424 |

FOREIGN PATENT DOCUMENTS

WO    WO 2006/110671 A2    10/2006

OTHER PUBLICATIONS

Grant, et al., "Use of the Proneview Helmet System with a Modified Table Platform for Open Access to the Eyes During Prone Spine Surgery". Anesthesia & Analgesia, vol. 103, No. 2, Aug. 2006, pp. 499-500.

* cited by examiner

*Primary Examiner* — Ranodhi Serrao
(74) *Attorney, Agent, or Firm* — Edward W. Callan (57) ABSTRACT

Apparatus that allows at least one feature of a patient's face to be observed while the patient is in a prone position includes a facial cushion, a video camera and a monitor. The facial cushion provides cranial support for a patient in a prone position during a medical procedure. The cushion has a frontal aperture that is dimensioned so that the facial feature of a patient wearing the facial cushion and in a prone position are visible through the at least one aperture. The video camera has a lens disposed for providing a sequence of video signals representing sequential images of the facial features that are visible through the frontal aperture. The monitor is coupled to the video camera for enabling the images of the at least one facial feature to be monitored. The images are monitored by a video monitor and/or a computer.

10 Claims, 10 Drawing Sheets

VIDEO OBSERVATION OF A PATIENT'S FACE DURING A MEDICAL PROCEDURE WHILE THE PATIENT IS IN A PRONE POSITION

BACKGROUND OF THE INVENTION

The present invention generally pertains to medical apparatus and is particularly directed to apparatus that allows various features of a patient's face, such as the eyes, nose and/or mouth, to be observed while the patient is in a prone position.

Such an apparatus is described in U.S. Pat. No. 6,490,737 to William Mazzei, Gregory Jordan and An Vu. The apparatus includes a facial cushion for providing cranial support for a patient during surgery. The facial cushion is dimensioned for achieving optimum fit and pressure diffusion upon the face of the patient. The facial cushion has a frontal aperture and viewing passages in the cushion sidewalls. The aperture and the viewing passages are so dimensioned and relatively disposed that the eyes, nose and mouth of a patient in the prone position and wearing the facial cushion may be seen through the viewing passages from positions adjacent to the sidewall viewing passages. In one embodiment, the apparatus further includes a mirrored surface, which is disposed beneath the cushion to enable upright individuals standing adjacent to the facial cushion to view images of the features of the patient's face that are visible through the aperture and reflected off of the mirrored surface.

SUMMARY OF THE INVENTION

The present invention provides apparatus for initiating an alert of a change in a feature of a patient's face while the patient is in a prone position during a medical procedure, comprising: a facial cushion for providing cranial support for a patient in a prone position during a medical procedure, wherein the cushion has at least one frontal aperture that is dimensioned so that at least one facial feature of a patient wearing the facial cushion and in a prone position is visible through the at least one aperture from beneath the patient; a video camera having a lens disposed for providing a sequence of video signals representing sequential images of the at least one facial feature that are visible through the at least one frontal aperture; and a computer coupled to the video camera for processing the video signals; wherein the computer is programmed (a) for processing the video signals to detect a change in at least one aspect of the sequential images of the at least one facial feature that exceeds a predetermined threshold while the facial cushion is providing cranial support for the patient in a prone position during a medical procedure, and (b) for initiating a alert when the predetermined threshold is exceeded.

The present invention enhances the ability of medical personnel, such as anesthesiologists and anesthetists, to meet a requirement of periodically recording in a surgical procedure file that they checked the patient's eyes every specified interval, typically every fifteen minutes, to ensure that no pressure from the facial cushion or any other material is impacting the patient's eyes. It becomes more difficult and inconvenient to periodically view the patient's facial features at the required times as the medical procedure becomes longer and longer. Some medical procedures in which the patient is in a prone position take at least ten hours. The present invention allows medical personnel to view the patient's facial features by looking at a video monitor, instead of stooping, looking in a mirror or having to get out of a chair to look around the patient's head to see that the patient's eyes are safely within the frontal aperture of the facial cushion with nothing touching them. The present invention also obviates the necessity of the medical personnel having to engage in a dangerous practice of poking around the patient's eyes with their fingers in order to make the periodically required observations.

Additional features of the present invention are described with reference to the detailed description of the preferred embodiments.

DETAILED DESCRIPTION

Figure 1:
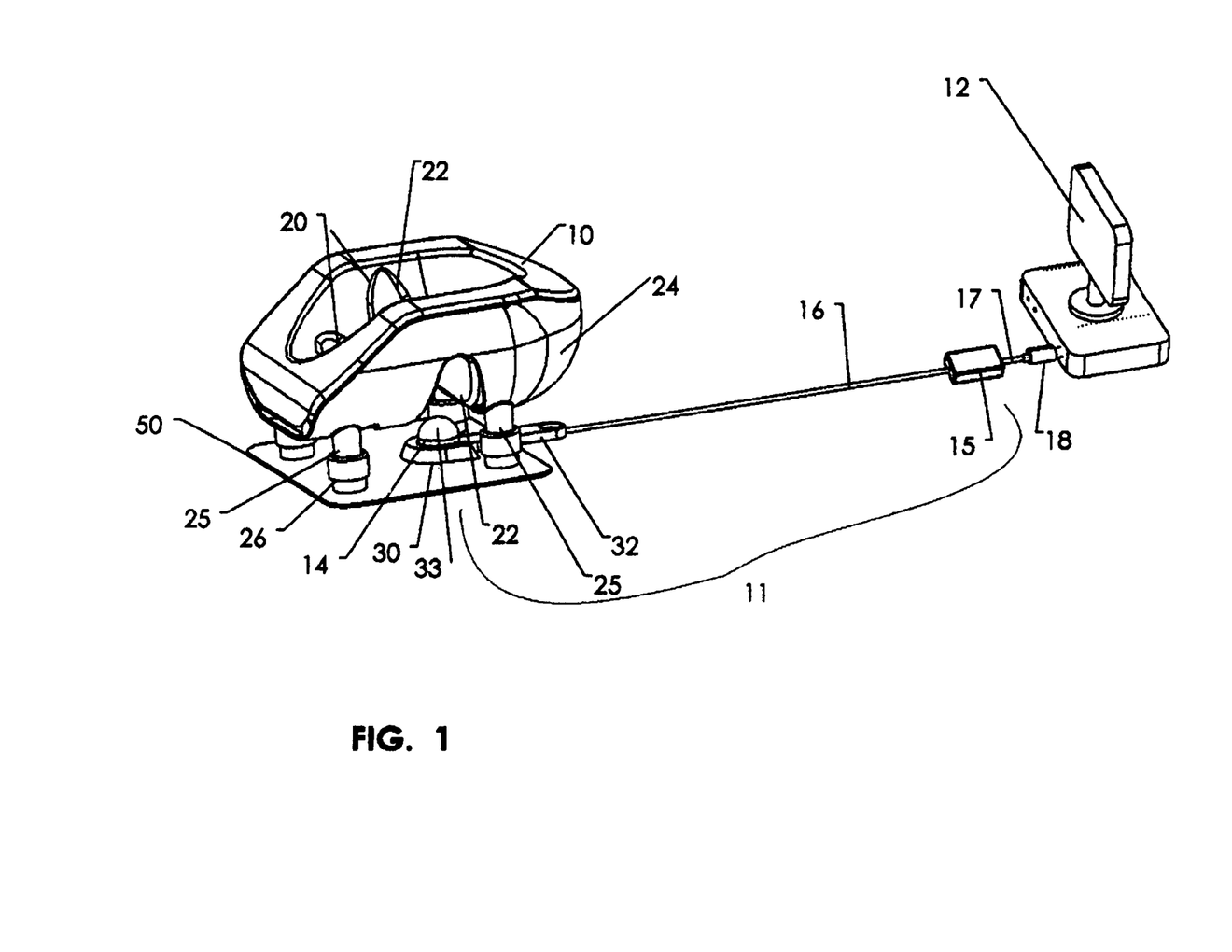
FIG. 1 is a perspective view of one embodiment of an apparatus according to the invention.
Figure 1A:
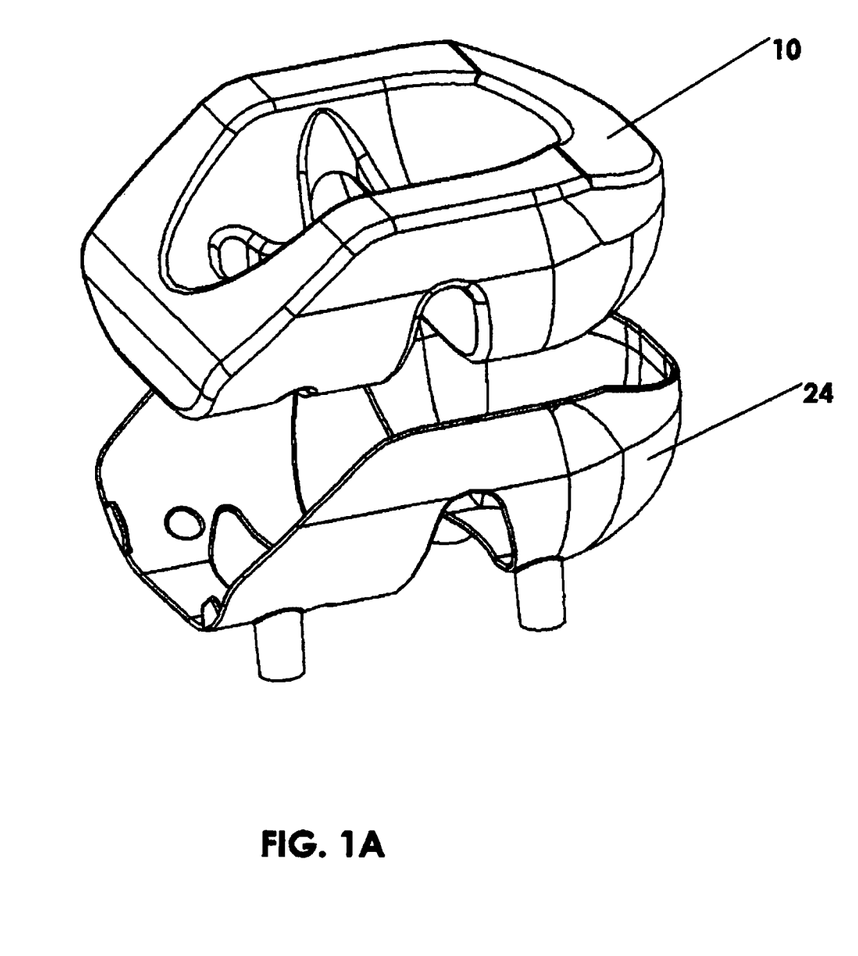
FIG. 1A is an exploded perspective view of the combination of the facial cushion and the cushion support in the embodiment shown in FIG. 1.
Figure 1B:
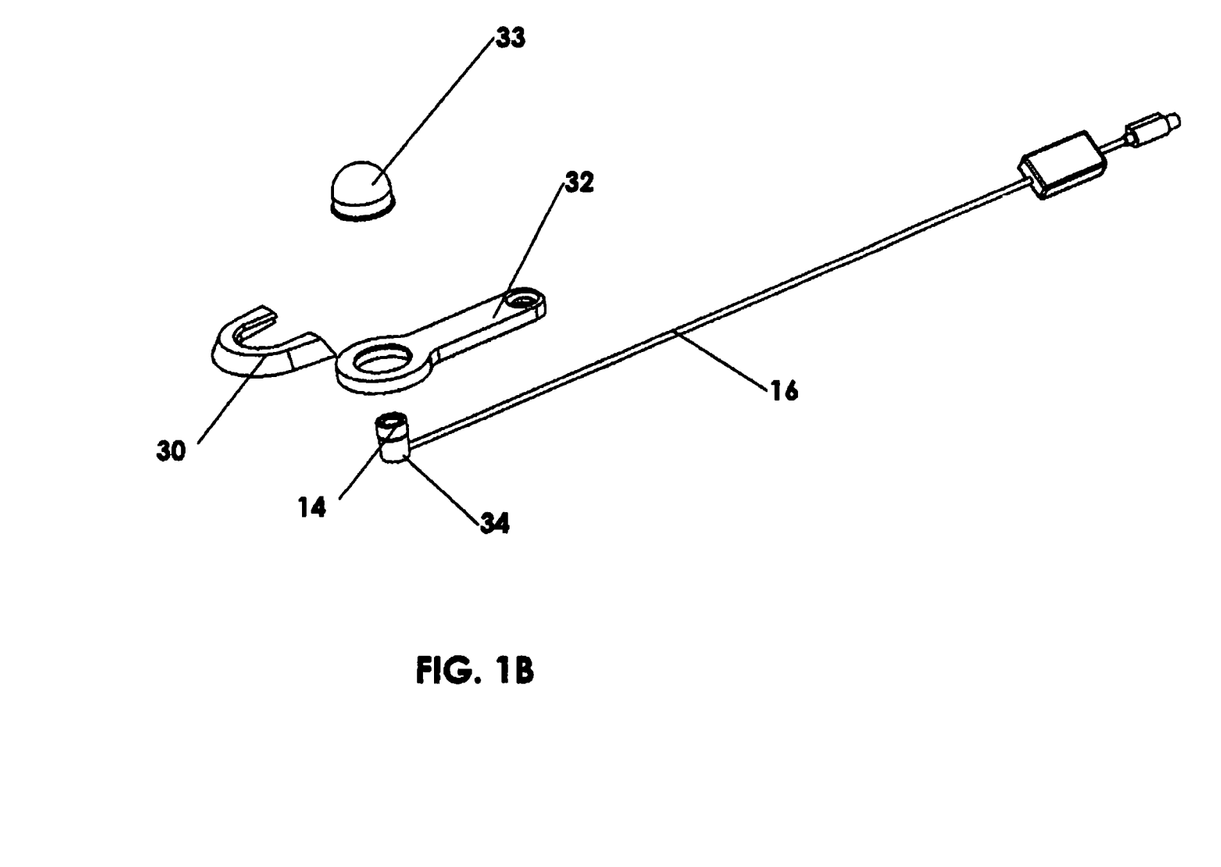
FIG. 1B is an exploded perspective view of the combination of the camera, a lens holder and a protective dome included in the embodiment shown in FIG. 1.

Referring to FIGS. 1, 1A and 1B, one embodiment of an apparatus according to the present invention includes a facial cushion 10, a video camera 11 and a video monitor 12. The video camera 11 includes a lens 14 and a video circuit box 15, which are interconnected by a first cable 16. The video circuit box 15 is connected to the video monitor 12 by a second cable 17 and a connector 18. The video camera 11 may be powered by a rechargeable battery (not shown) or otherwise, such as via a line from a wall socket.

In the preferred embodiments, the video camera 11 is an audio video camera that includes a microphone (not shown), and provides color images. In alternative embodiments, a microphone is not included in the video camera 11 and/or the video camera 11 provides monochromatic images.

The facial cushion 10 provides cranial support for a patient in a prone position during a medical procedure. The facial cushion 10 is dimensioned for achieving optimum fit and pressure diffusion upon the face of the patient.

The facial cushion 10 has a frontal aperture 20, which includes viewing passages 22 in the cushion sidewalls. The frontal aperture 20 is dimensioned so that the eyes, nose and mouth of a patient wearing the facial cushion 10 and in a prone position are visible through the frontal aperture 20 from beneath the patient. The viewing passages 22 of the frontal aperture 20 are so dimensioned and disposed that the eyes, nose and mouth of a patient in the prone position and wearing the facial cushion may be seen though the viewing passages 22 from positions adjacent to the sidewall viewing passages 22. The facial cushion 10 may be made of one component or a plurality of components.

The facial cushion 10 is supported by a rigid casing 24. The support casing 24 has four legs 25, which are mounted in four hollow posts 26 that extend from a platform 28; whereby the casing 24 supports the facial cushion 10 in a stationary position above the platform 28. The support casing 24 includes an aperture 29 that is compatible with the frontal aperture 20 of the facial cushion 10.

Various alternative embodiments of facial cushions and support casings are described in the aforementioned U.S. Pat. No. 4,635,625, the disclosure of which is incorporated herein by reference thereto. In said patent the term "helmet" is used to refer to the support casing.

The platform 28 may be a table, such as an operating table. In some embodiments, the platform 28 can be attached off the end of any operating table or off the sides or on the rails of an operating table.

The video camera lens 14 is disposed beneath the facial cushion 10 for providing a sequence of video signals representing sequential images of the facial features that are visible through the frontal aperture 20. In various alternative embodiments, the sequence of video signals represent relatively continuous images or time-lapsed images, such as images at five-minute intervals, as determined by a timer in the video camera circuit box 15.

When the setting has relatively low ambient lighting, a camera having a low lux rating may be used, and/or a light source (not shown) can be provided to enhance the clarity of the images. Such a light source, such as an LED or an infrared source, may be attached to the video camera 11 adjacent to the camera lens 14.

A receptacle 30 is disposed on the platform 28 for locating the camera lens 14 in a stationary position beneath the facial cushion 10. The camera lens 14 is held in the stationary position by a lens holder 32. The lens holder 32 is slid into the receptacle 30 so that the lens 14 and the facial cushion 10 are held in a stationary relationship to one another.

The lens 14 is covered by a transparent dome 33 for shielding the lens 14 from fluids secreted by a patient wearing the facial cushion 10 and in the prone position above the lens 14.

In the preferred embodiments, the camera lens 14 is a wide angle lens for providing a relatively undistorted image of at least the portion of the patient's face that extends laterally to fully include both eyes. A preferred wide angle lens is a 1.9 mm super wide angle lens having a focal length of at least one inch.

In some preferred embodiments, the first cable 16 passes through the side of a casing 34 for the lens 14; and the lens casing 34 has a flat bottom so that the camera lens 14 can be readily disposed in a stable position on a flat surface.

The video monitor 12 is coupled to the video camera 11 for enabling the images of the visible facial features represented by the video signals provided by the video camera 11 to be monitored in real time. Preferably, the video monitor 12 is located so that it can be viewed by medical personnel having the responsibility of observing the various features of the patient's face during the medical procedure in order to detect any change in such features that could be detrimental to the patient, such as a movement of the patient's face relative to the facial cushion 10 that causes any part of the eyes to be impacted by the facial cushion 10 or some other device in the proximity. A person, typically an anesthetist or an anesthesiologist, views the video monitor 12 at least periodically during the course of the medical procedure and makes a periodic record of the status of the facial features observed on the video monitor 12.

In addition to monitoring a patient's eyes, the patient's mouth and/or nose are also monitored by use of the video monitor 12 to make sure that the patient's air passages are not obstructed and/or that tubing inserted into the patient's air passages have not been removed therefrom and/or that such tubing has not become disconnected from a breathing circuit.

Figure 2:
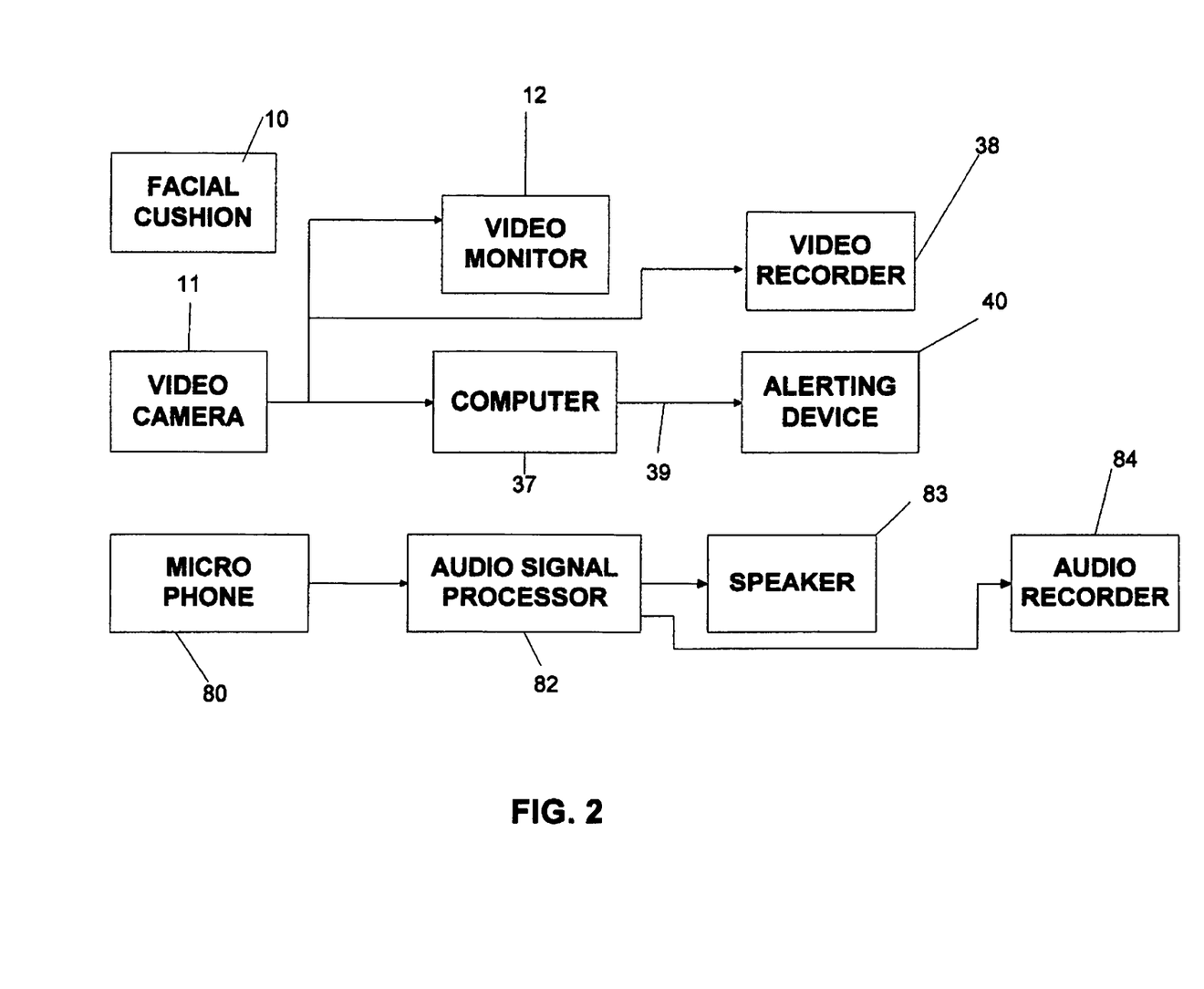
FIG. 2 is a block diagram of an embodiment of the invention in which a video monitor, a computer and a video recorder are coupled to the video camera.

Referring to FIG. 2, in various alternative embodiments, video signals 36 representing sequential images of the facial features observed from beneath the facial cushion 10 are provided by a video camera 11 disposed beneath the facial cushion 10 to a video monitor 12, a computer 37 and/or a video recorder 38. The video monitor 12, the computer 37 and the video recorder 38 are respectively coupled to the video camera 11 by a wireless interface or by a hardwired connection.

The computer 37 is programmed for processing the video signals to detect a change in at least one aspect of the sequential images that exceeds a predetermined threshold and, when the predetermined threshold is exceeded, to provide a signal 39 to a device 40 that alerts the medical personnel to such a detected change.

Figure 3:
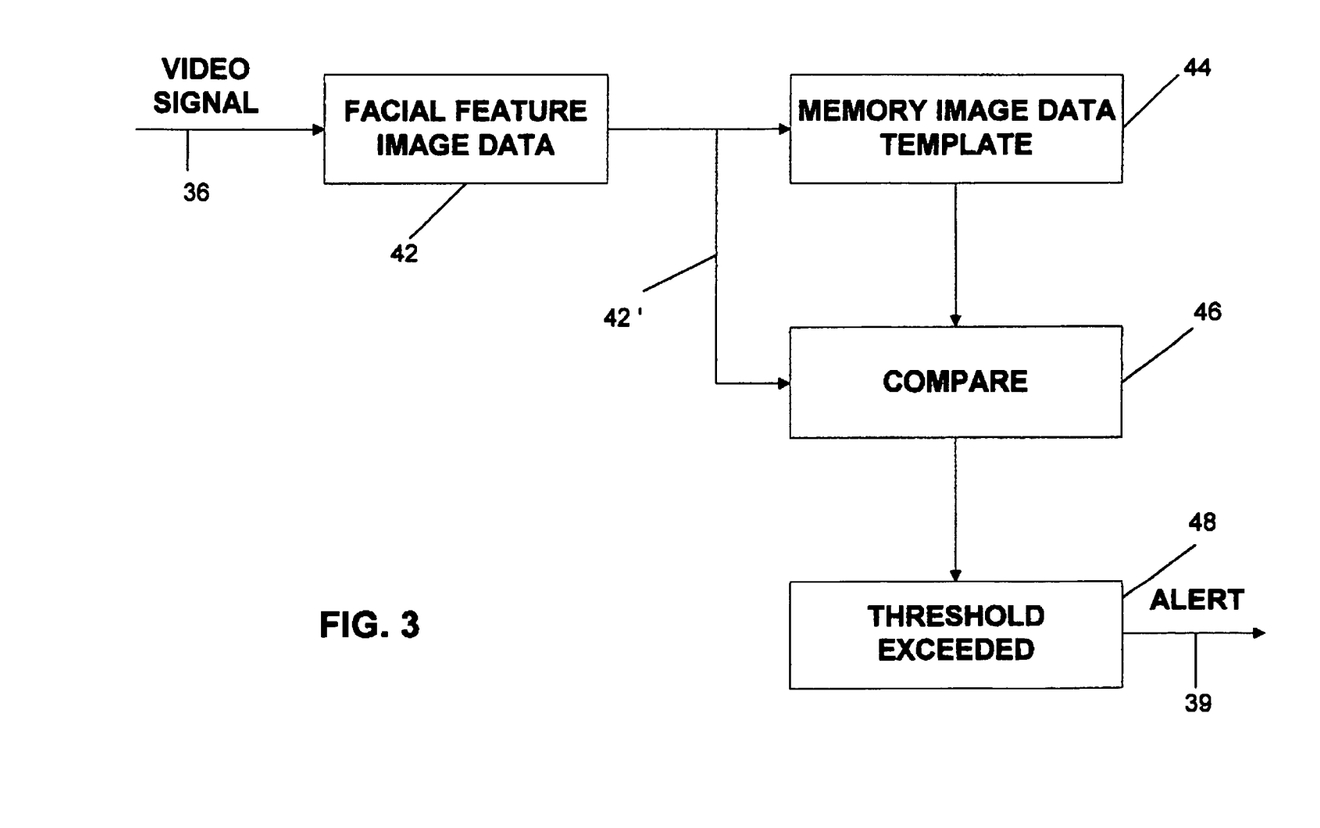
FIG. 3 is a block diagram of an embodiment of signal processing by the computer included in the embodiment shown in FIG. 2.

Referring also to FIG. 3, the video signals 36 are processed by the computer 37 to provide facial-feature-image data 42. The initial facial-feature-image data 42 is stored as an image data template in a memory 44 of the computer 37. The computer 37 performs a routine 46 of comparing the stored image data template in the memory 44 to facial-feature-image data 42' provided by processing the subsequent sequential video signals 36 from the video camera 11 in order to detect a change in at least one aspect of the sequential images that exceeds the predetermined threshold. Facial recognition software may used to implement this feature.

Whenever the predetermined threshold is exceeded, as shown at 48, the computer 37 provides the signal 39 to the device 40 that alerts a person to such a detected change. The alert is of an audible, visual and/or vibratory nature. The alert is provided to the person having the responsibility of observing the various features of the patient's face during the medical procedure. After an alert has been provided and the patient's face is once again placed in a desired position relative to the facial cushion 10, the image data template that is stored in the memory 44 is once again initialized.

The video recorder 38 records the video signals provided by the video camera 11 to provide a record of the sequential images of the visible facial features over the duration of the medical procedure in which the patient is wearing the facial cushion and in a prone position. The recorded images may be time-lapsed images to limit the amount of memory required to preserve the record of the sequential images. The recorded images may be used to corroborate the records made by a person viewing the video monitor 12 during the course of the medical procedure. The recorded images may be downloaded from the video recorder 38 to a portable data storage device, such as disc or a memory stick, that can be put into the patient's file.

In some embodiments, the platform 28 has a mirrored upper surface 50. The mirrored surface 50 is disposed beneath the facial cushion 10 to enable upright individuals standing adjacent to the facial cushion 10 to view images of the features of the patient's face that are reflected off of the mirrored surface 50. The receptacle 30 holds the video camera lens 14 in a stationary position on the mirrored surface 50. This mirrored surface feature provides an additional way to observe the facial features of the patient in the event that for some reason the display of the facial features on the video monitor 12 is interrupted.

Figure 4:
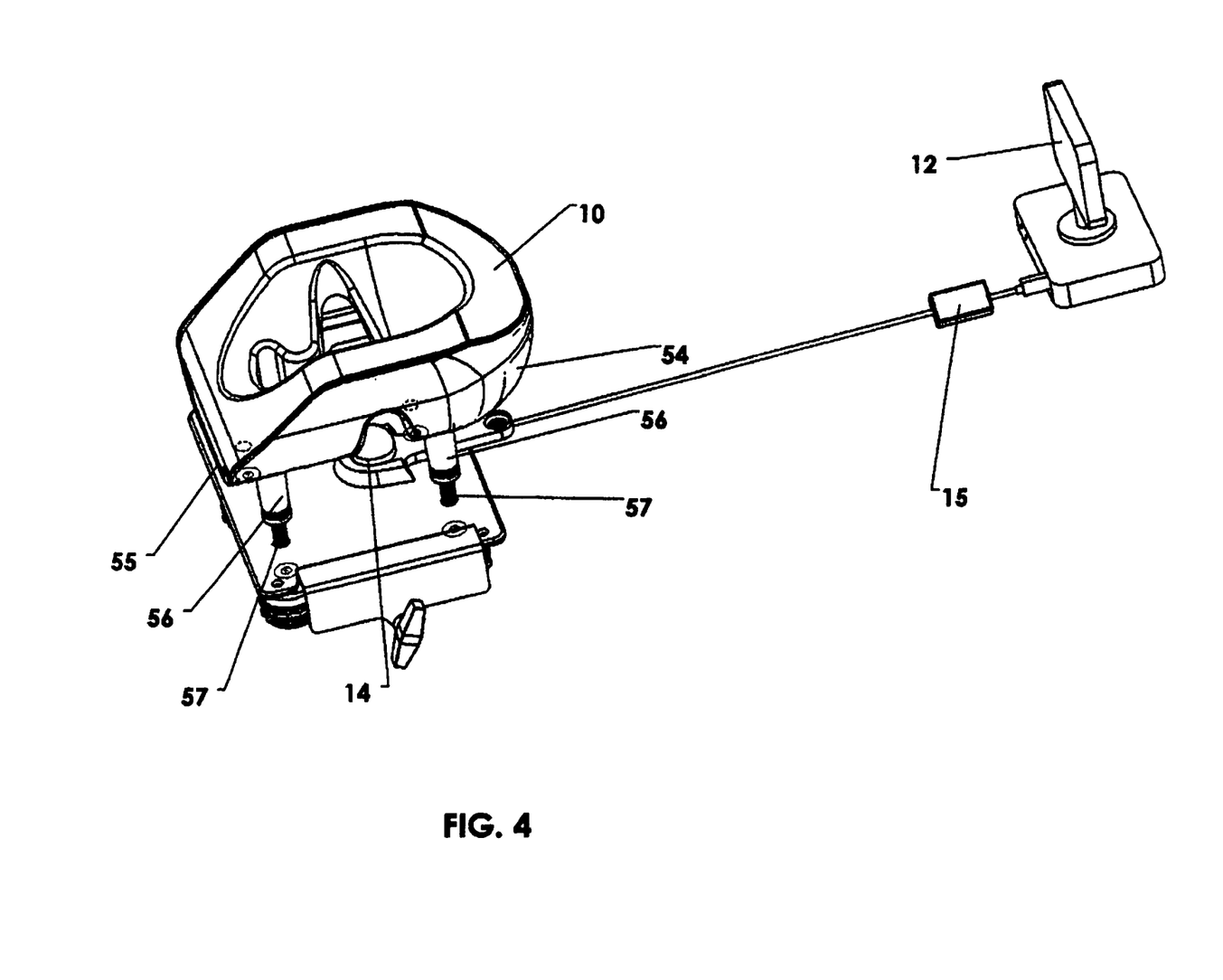
FIG. 4 is a perspective view of another embodiment of an apparatus according to the invention.

Referring to FIG. 4, in another embodiment of the apparatus of the present invention, a cushion support casing 54 is mounted on a platform 55 of a Jackson operating table. The support casing 54 has four hollow legs 56, which are mounted on four posts 57 that extend from the platform 55. In other aspects, the embodiment of FIG. 4 has the same alternative features as described above with reference to FIGS. 1, 1A, 1B, 2 and 3.

Figure 5:
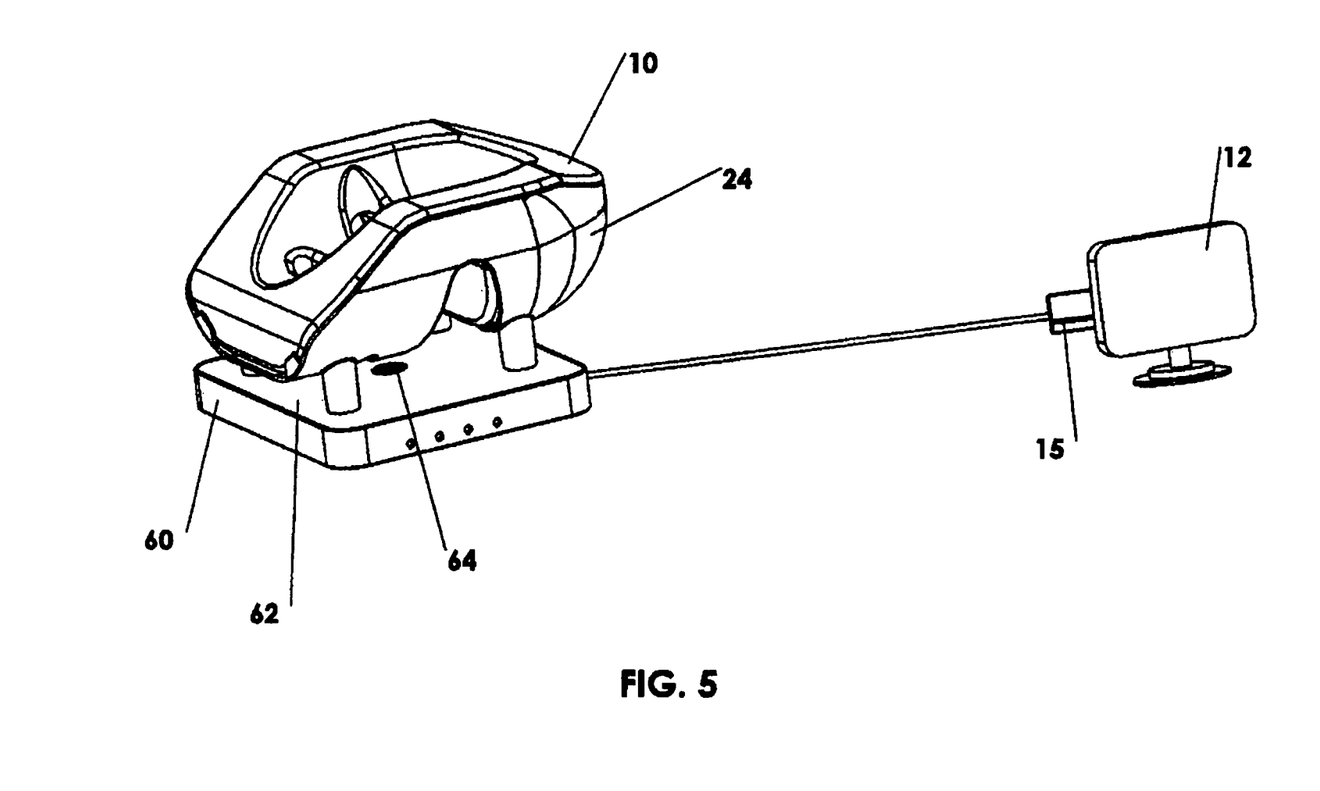
FIG. 5 is a perspective view of still another embodiment of an apparatus according to the invention.

Referring to FIG. 5, in still another embodiment of the apparatus of the present invention, the support casing 24 is mounted on a platform 60 that has a mirrored surface 62 and a chamber (not shown) beneath the mirrored surface 62 in which the video camera is contained so that the camera lens 64 is disposed amidst the mirrored surface 62 in a position beneath the frontal aperture 20 of the facial cushion 10. In other aspects, the embodiment of FIG. 5 has the same alternative features as described above with reference to FIGS. 1, 1A, 1B, 2 and 3.

Figure 6:
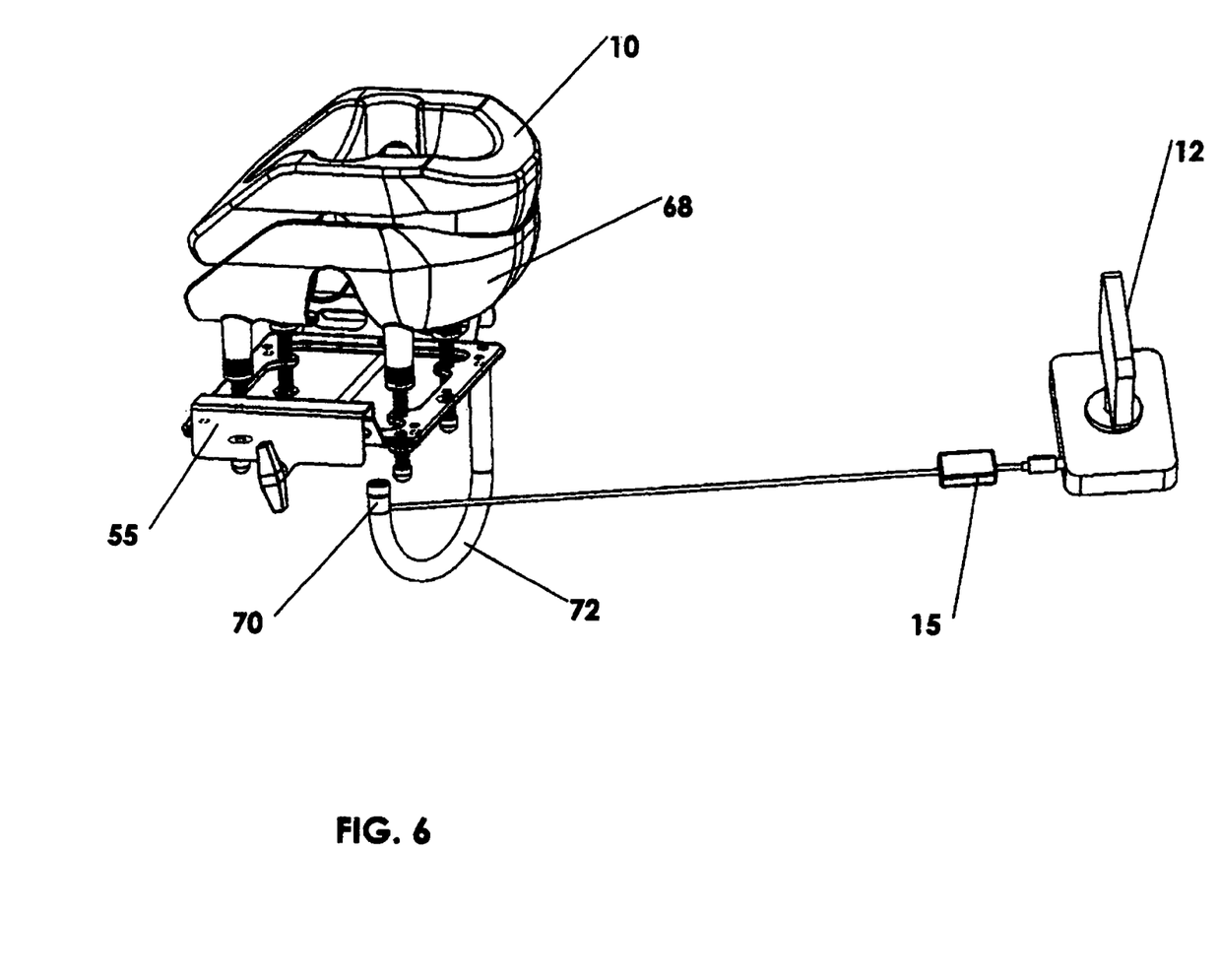
FIG. 6 is a perspective view of yet another embodiment of an apparatus according to the invention.

Referring to FIG. 6, in yet another embodiment of the apparatus of the present invention, a cushion support casing 68 is mounted on a platform 55 of a Jackson operating table, as described above with reference to FIG. 4; and a video camera lens 70 is disposed at the end of a flexible arm 72 that is attached to the cushion support casing 68. In other aspects, the embodiment of FIG. 6 has the same alternative features as described above with reference to FIGS. 1, 1A, 1B, 2 and 3.

Figure 7:
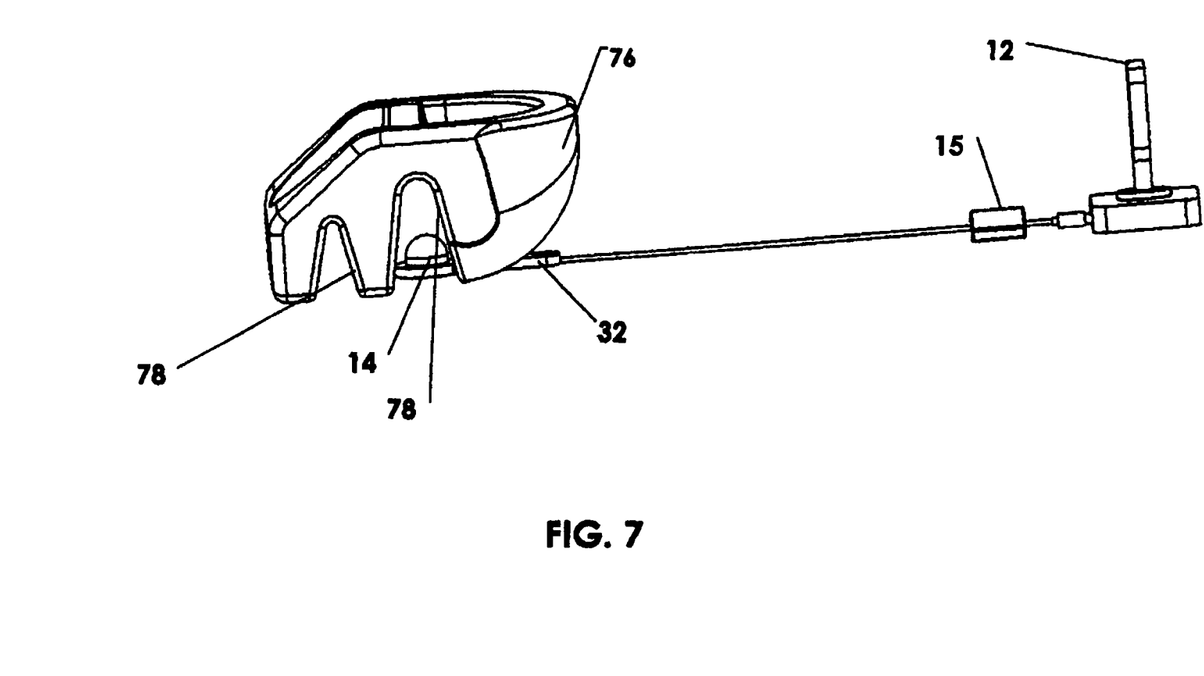
FIG. 7 is a view of a further embodiment of an apparatus according to the invention.
Figure 7A:
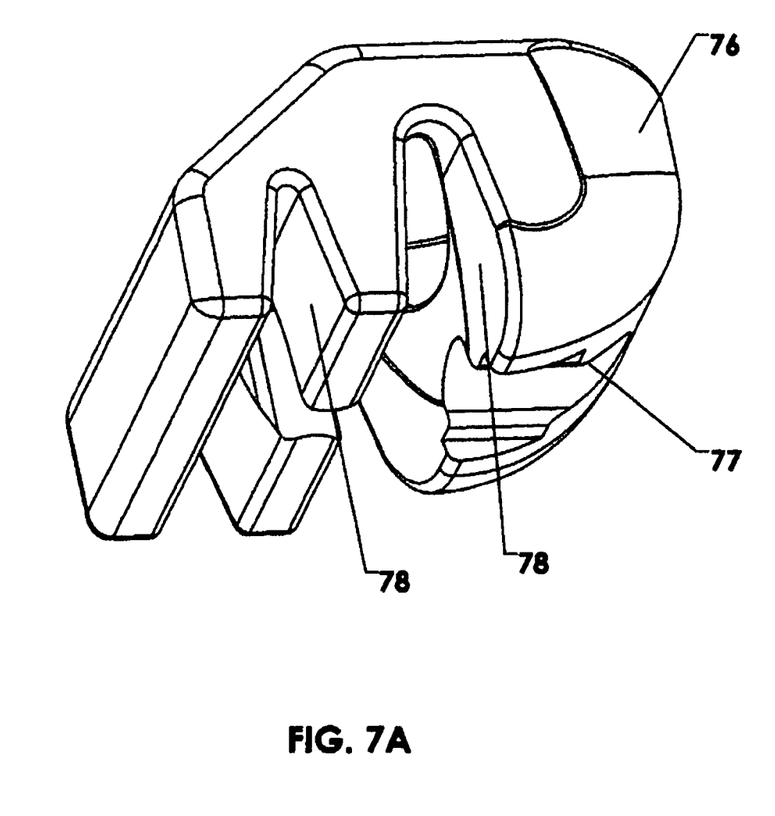
FIG. 7A is a perspective view of the facial cushion included in the embodiment shown in FIG. 7.

Referring to FIGS. 7 and 7A, a further embodiment of the apparatus of the present invention does not include a cushion support casing; and the facial cushion 76 is self-supporting and configured for mounting on a platform (not shown). The platform may be as described with reference to the embodiments shown in FIG. 1, 4, 5 or 6. The facial cushion 76 has a frontal aperture 77, which includes viewing passages 78 in the cushion sidewalls. The facial cushion 76 is made of one component. The self-supporting facial cushion may have a different configuration than the facial cushion 76 shown in FIGS. 7 and 7A. An example of a self-supported facial cushion having a different configuration that may be used in this further embodiment of the apparatus of the present invention is the GentleTouch brand pillow, which presently is a product of Mizuho OSI. In other aspects, the embodiment of FIGS. 7 and 7A has the same alternative features as described above with reference to FIGS. 1, 1A, 1B, 2 and 3.

Referring again to FIG. 2, the apparatus of the present invention may be used in combination with an audio system for allowing the breathing of a patient to be monitored while the patient is wearing the facial cushion and in the prone position. The audio system includes a microphone 80, an audio signal processor 82 and a speaker 83. The audio signal processor 82 is coupled to the microphone 80 by a wireless or hardwired interface.

The microphone 80 is disposed for detecting the breathing of the patient while the patient is wearing the facial cushion and in the prone position. In one embodiment, the microphone 80 is disposed in the video camera 11. In an alternative embodiment, the microphone 80 is disposed adjacent the platform 28, which is shown in FIG. 1. The audio signal processor 82 processes the signals received from the microphone 80. The speaker 83 is coupled to the audio signal processor 82 to reproduce the sounds of the patient's breathing.

The speaker 83 is located so that the sounds of the patient's breathing can be heard by medical personnel having the responsibility of monitoring the patient's breathing during the medical procedure. The speaker 83 may be included in a headset or contained in a casing that is disposed on a table or the like; or the speaker casing is configured for being attached to a person or some object, such as a wall or some apparatus, such as an operating table. The speaker 83 is coupled to the audio signal processor 82 by a wireless or hardwired interface.

An alternative embodiment of the audio system also includes an audio recorder 84, which is coupled to the audio signal processor 82 for making an audio record of the patient's breathing during a medical procedure while the patient is wearing the facial cushion and in the prone position. The audio record may be used to corroborate the video recording made by the video recorder 38.

In an embodiment in which the microphone 80 is included in the video camera 11, the audio signal processor 82 is included in the circuit box 15 of the video camera, the speaker 83 is included with the video monitor 12 in a television monitor and/or the audio recorder 84 is included in the video recorder 38.

In an embodiment that includes the computer 37 and the alerting device 40, the speaker 83 and the alerting device 40 can be integrated to provide an audible alert when the computer 37 detects that the predetermined threshold is exceeded, as shown at 48 in FIG. 3.

In further alternative embodiments (not shown), (a) the video camera lens is disposed for viewing images that are reflected off of a mirror or off of two mirrors; (b) the video camera lens is mounted inside the cushion support casing or inside the facial cushion; and/or (c) the video camera lens is mounted on adjustment screws to travel with an extension to provide an optimum focal point.

In still other embodiments the various aspects of the different embodiments described herein are combined with one another to the extent that they are not incompatible with each other.

The benefits specifically stated herein do not necessarily apply to every conceivable embodiment of the present invention. Further, such stated benefits of the present invention are only examples and should not be construed as the only benefits of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. Apparatus for initiating an alert of a change in a feature of a patient's face while the patient is in a prone position during a medical procedure, comprising:

a facial cushion for providing cranial support for a patient in a prone position during a medical procedure, wherein the cushion has at least one frontal aperture that is dimensioned so that at least one facial feature of a patient wearing the facial cushion and in a prone position is visible through the at least one aperture from beneath the patient;

a video camera having a lens disposed for providing a sequence of video signals representing sequential images of the at least one facial feature through the at least one frontal aperture; and a computer coupled to the video camera for processing the video signals;

wherein the computer is programmed (a) for processing the video signals to detect a change in at least one aspect of the sequential images of the at least one facial feature that exceeds a predetermined threshold while the facial cushion is providing cranial support for the patient in a prone position during a medical procedure, and (b) for initiating a alert when the predetermined threshold is exceeded.

2. Apparatus according to claim 1, wherein the at least one frontal aperture is dimensioned so that at least the eyes of a patient wearing the cushion can be observed through the at least one frontal aperture.

3. Apparatus according to claim 2, wherein the lens is a wide angle lens for providing a relatively undistorted image of a portion of the patient's face that extends laterally to fully include both eyes.

4. Apparatus according to claim 1 in combination with:
an audio system for allowing the breathing of a patient to be monitored while the patient is wearing the facial cushion and in a prone position.

5. The combination according to claim 4, wherein the audio system includes a microphone disposed for detecting the breathing of the patient while the patient is wearing the facial cushion and in the prone position.

6. Apparatus according to claim 1, wherein the at least one facial feature is at least one of the patient's eyes.

7. Apparatus according to claim 6, wherein the predetermined threshold is exceeded when the image of at least one of the patient's eyes that is represented by the video signals that are processed by the computer while the facial cushion is providing cranial support for a patient in a prone position during a medical procedure, include an image of the patient's eyes being impacted by pressure from the facial cushion or any other material.

8. A nontransitory computer readable storage medium for use with a computer in apparatus for initiating an alert of a change in a feature of a patient's face while the patient is in a prone position during a medical procedure, said apparatus comprising: a facial cushion for providing cranial support for a patient in a prone position during a medical procedure, wherein the cushion has at least one frontal aperture that is dimensioned so that at least one facial feature of a patient wearing the facial cushion and in a prone position is visible through the at least one aperture from beneath the patient; a video camera having a lens disposed for providing a sequence of video signals representing sequential images of the at least one facial feature through the at least one frontal aperture; and a computer coupled to the video camera for processing the video signals;

wherein the computer readable storage medium includes computer executable program instructions for causing the computer to perform and/or enable the steps of:
(a) processing the video signals to detect a change in at least one aspect of the sequential images of the at least one facial feature that exceeds a predetermined threshold while the facial cushion is providing cranial support for the patient in a prone position during a medical procedure, and
(b) initiating a alert when the predetermined threshold is exceeded.

9. A nontransitory computer readable storage medium according to claim 8, wherein the at least one facial feature is at least one of the patient's eyes.

10. A nontransitory computer readable storage medium according to claim 8, wherein the predetermined threshold is exceeded when the image of at least one of the patient's eyes that is represented by the video signals that are processed by the computer while the facial cushion is providing cranial support for a patient in a prone position during a medical procedure, include an image of the patient's eyes being impacted by pressure from the facial cushion or any other material.

* * * * *

UNITED STATES PATENT AND TRADEMARK OFFICE
CERTIFICATE OF CORRECTION

PATENT NO. : 8,648,900 B2
APPLICATION NO. : 11/867242
DATED : February 11, 2014
INVENTOR(S) : An Binh Vu and Gregory Philip Jordan It is certified that error appears in the above-identified patent and that said Letters Patent is hereby corrected as shown below:

In the Specification:

at column 1, line 44, "that are visible" should be omitted.

Signed and Sealed this
Twenty-ninth Day of July, 2014

Michelle K. Lee
*Deputy Director of the United States Patent and Trademark Office*